United States Patent [19]
Ruf

[11] Patent Number: 5,055,603
[45] Date of Patent: Oct. 8, 1991

[54] METHOD FOR THE PREPARATION OF DIALKYL-TIN-DICHLORIDES

[75] Inventor: Erich Ruf, Essen-Haarzopf, Fed. Rep. of Germany

[73] Assignee: Th. Goldschmidt AG, Essen, Fed. Rep. of Germany

[21] Appl. No.: 648,574

[22] Filed: Jan. 31, 1991

[30] Foreign Application Priority Data

Mar. 12, 1990 [DE] Fed. Rep. of Germany ....... 4007745

[51] Int. Cl.$^5$ ................................................. C07F 7/22
[52] U.S. Cl. ..................................... 556/102; 556/90; 556/95
[58] Field of Search ............................ 556/90, 95, 102

[56] References Cited

U.S. PATENT DOCUMENTS 3,036,103  5/1962  Johnson ............................ 260/429.7
3,287,386 11/1966  Neumann ......................... 260/429.7

FOREIGN PATENT DOCUMENTS 0158163 10/1985 European Pat. Off. ............. 556/95
1157617 11/1963 Fed. Rep. of Germany ...... 556/102

Primary Examiner—José G. Dees
Assistant Examiner—Porfirio Nazario-Gonzalez
Attorney, Agent, or Firm—Toren, McGeady & Associates

[57] ABSTRACT

A method is disclosed for the production of dialkyl-tin-dichlorides whose alkyl groups have 1 to 22 carbon atoms. Trialkyl-aluminum is slowly added to a solution of tin-diacetate-dichloride and tetrahydrofuran in the mole ratio of about 2:3. The aluminum-triacetate precipitating during the reaction is removed by filtration and the tetrahydrofuran used as solvent is removed by distillation.

3 Claims, No Drawings

METHOD FOR THE PREPARATION OF DIALKYL-TIN-DICHLORIDES

FIELD OF INVENTION

The invention generally relates to organic tin compounds and is particularly directed to a method for the preparation of dialkyl-tin-dichlorides whose alkyl groups each contain 1 to 22 carbon atoms.

Pursuant to the prior art, essentially two methods are known for the production of dialkyl-tin-dichlorides, namely, the Grignard method and the alkylaluminum method.

Both methods have in common that in a first method stage, tetraalkyl-tin is first produced while, in a second method stage, alkyl-tin-chloride is prepared by comproportionation of the tetraalkyl-tin with tin-(IV)-chloride.

The state of the art may be depicted as follows:

First Method Step (a) Grignard method

(b) alklyl-aluminum method

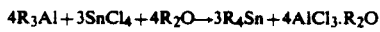

Second Method Step

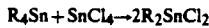

The comproportionation of 1 mole of tetraalkyl-tin with 1 mole of tin-(IV)-chloride, indicated above as an example, leads from a practical point of view to a mixture of alkyl-tin-chlorides from which the individual alkyl-tin-chlorides are recovered by fractional distillation.

Both method stages take place at high temperatures. In the Grignard method, the presence of solvent and, in the alkylaluminum method, the presence of complex forming agents such as, for example, dibutylether, are necessary for the required complex formation of the aluminum-chloride which is formed in the reaction.

OBJECT OF THE INVENTION

It is the primary object of the invention to provide a method for the production of dialkyl-tin-dichlorides which is superior to prior art procedures, is simple to carry out and results in high yields.

It is also an object of the invention to provide a method of the indicated kind which proceeds smoothly in a one-stage reaction and at low temperatures.

Generally, it is an object of the invention to improve on the art of producing dialkyl-tin-dichlorides.

SUMMARY OF THE INVENTION

Briefly, and in accordance with the invention, dialkyl-tin-dichloride is produced by adding trialkyl-aluminum slowly to a solution of tin-diacetate-dichloride in tetrahydrofuran in a mole ratio of about 2:3. The aluminum-triacetate which precipitates during the course of the reaction is removed by filtration, while the tetrahydrofuran used as solvent is removed by distillation.

The alkyl groups of the trialkyl-aluminum, used as starting material, are linear or branched and each has 1 to 22 carbon atoms. Linear alkyl groups are preferred. Trialkyl-aluminum compounds in which the three alkyl groups are the same are particularly preferred. Examples of suitable alkyl groups are methyl, ethyl, propyl, i-propyl, butyl, i-butyl, octyl, ethylhexyl, decyl, stearyl and behenyl.

During the partial alkylation of tin-diacetate-dichloride with trialkyl-aluminum pursuant to the inventive method, only the acetate groups are alkylated under simultaneous formation of aluminum-triacetate corresponding to the equation:

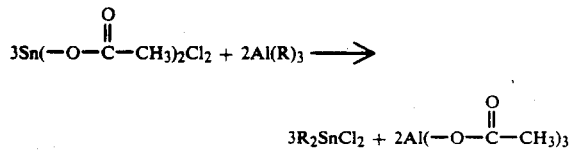

BRIEF DESCRIPTION OF PREFERRED EMBODIMENTS

A preferred embodiment of the inventive method is characterized in that the reaction mixture, during the addition of the trialkyl-aluminum, has a temperature of about 5° to 60° C. Advantageously, the reaction mixture during the addition of the trialkyl-aluminum is maintained at a temperature of about 10° to 40° C. Since the reaction proceeds exothermally, the reaction mixture generally has to be cooled to maintain the indicated temperature range.

If tetrahydrofuran is replaced by other solvents or liquid hydrocarbons such as, for example, diethylether, dibutylether, mono- and diglyme as well as toluene, the partial alkylation does not proceed in the same pronounced manner as with tetrahydrofuran and larger amounts of by-products are usually formed. Tetrahydrofuran is therefore the preferred solvent.

It will be appreciated that the inventive method has substantial advantages as compared to the state of the art as indicated above. Since it is a direct, one-step process, the preceding preparation of tetraalkyl-tin and subsequent comproportionation of tetraalkyl-tin with tin-(IV)-chloride are rendered unnecessary.

The dialkyl-tin-dichlorides obtained pursuant to the inventive method are suitable for improving glass surfaces and are also useful as intermediaries in the production of tin organic compounds.

The aluminum-triacetate formed as by-product is a valuable catalyst in reesterification, esterification and polycondensation reactions.

The invention will now be described by several examples, it being understood that these examples are given by way of illustration and not by way of limitation.

EXAMPLE 1

This experiment was carried out in a 250 ml four neck flask fitted with a stirrer, drop funnel, cooler with argon supply and thermometer. 61.6 gram of tin-diacetate-dichloride and 92 gram of tetrahydrofuran were added to the flask.

The product mixture is stirred for 10 minutes and a clear solution is obtained in this manner. 26.4 gram (stoichiometric amount) of triisobutyl-aluminum is added to the solution in dropwise manner and while stirring. The addition is conducted in such a manner that the temperature of the product mixture is maintained at about 30° C. The addition time, in dropwise manner, amounted to about 25 minutes.

Aluminum-triacetate preciptates. The acetate is removed by filtration through a sintered glass disc connectable to a vacuum source and is washed four times with about 100 ml tetrahydrofuran each time. The aluminum-triacetate so washed is dried in the filtering device under vacuum (1 to 3 mbar) at room temperature. 27.2 gram of aluminum-triacetate were obtained.

The entire wash liquor is combined with the filtrate. The clear solution thus obtained is subjected in a water jet vacuum (about 18 mbar) to distill off the tetrahydrofuran.

Finally, the diisobutyl-tin-dichloride obtained was distilled in an oil pump vacuum (1 to 3 mbar).

The yield, calculated on the distilled product, amounted to 51.6 gram of diisobutyl-tin-dichloride.

EXAMPLE 2

This experiment was carried out in a 250 ml four neck flask fitted with a stirrer, drop funnel, cooler with argon supply and thermometer. 61.5 gram of tin-diacetate-dichloride and 92.2 gram of tetrahydrofuran were added to the flask.

By stirring the product mixture, a clear solution was obtained within 10 minutes. 51.3 gram of trioctyl-aluminum (5% excess) were added to the solution under stirring and in dropwise manner. The addition time by drops was about 1 hours.

Aluminum-triacetate precipitated which, through a filter disc connectable to a vacuum source, was removed by filtration and was subsequently washed 4 times with about 100 ml tetrahydrofuran each time. The washed aluminum-triacetate was dried in the filtering device under vacuum conditions (1 to 3 mbar) and at room temperature. 26.3 gram of aluminum-triacetate were obtained.

The entire wash liquor was combined with the filtrate. The solution thus obtained was distilled in a water jet vacuum (about 18 mbar) to remove tetrahydrofuran. Subsequently, distillation in an oil pump vacuum (1 to 3 mbar) was carried out. In this manner, a distillation first running recovery of 4.1 gram at a distillation temperature of about 136° C. and 75.9 distillation main amount at a temperature of 149° to 153° C. were obtained.

The pre- or first running distillation amount comprises monooctyl-tin-trichloride and dioctyl-tin-trichloride in substantially equal amounts. The main distillation amount consists of dioctyl-tin-dichloride.

The yield was 2.05 gram of monooctyl-tin-trichloride and 77.95 gram of dioctyl-tin-dichloride.

EXAMPLE 3

This experiment was carried out in a 250 ml four neck flask fitted with a stirrer, drop funnel, cooler and argon supply as well as a thermometer. 61.5 gram of tin-diacetate-dichloride and 92.2 gram of tetrahydrofuran were added to the flask.

The product mixture was stirred and, within 10 minutes, a clear solution was obtained.

74.9 gram of tridodecyl-aluminum was added to this solution in dropwise manner under stirring in such a manner that the temperature of the reaction mixture amounted to about 40° C. Aluminum-triacetate precipitated. The precipitated aluminum-triacetate is removed by filtration at 50° C. through a sintered glass disc connectable to a vacuum source. Subsequently the product is washed 4 times about 100 ml tetrahydrofuran each time, the tetrahydrofuran having a temperature of about 50° C. The aluminum-triacetate obtained in this manner is dried in the filtering device under vacuum (1 to 3 mbar) at room temperture. 28.5 gram of aluminum-triacetate were obtained.

The wash liquor thus obtained is combined with the filtrate. Tetrahydrofuran is removed by distillation in a water jet vacuum (about 18 mbar). Subsequently, the didodecyl-tin-dichloride formed is distilled in an oil pump vacuum (<1 mbar/Kp: about 220° C.).

The yield was 99.6 gram of didodecyl-tin-dichloride.

I claim:

1. A method for the production of dialkyl-tin-dichloride, wherein each alkyl group has 1 to 22 carbon atoms, comprising:
   (a) adding trialkyl-aluminum slowly to a solution of tin-diacetate-dichloride in tetrahydrofuran in a mole ratio of about between 2:3, whereby aluminum-triacetate precipitates;
   (b) removing the precipitated aluminum-triacetate formed in the reaction by filtration; and
   (c) removing the tetrahydrofuran by distillation.

2. The method as claimed in claim 1, wherein step (a) is carried out such that the reaction mixture, during the addition of the trialkyl-aluminum, has a temperature of about between 5° to 60° C.

3. The method as claimed in claim 1, wherein the reaction mixture, during the addition of the trialkyl-aluminum, is maintained at a temperature of about between 10° to 40° C.

* * * * *